(12) United States Patent
Tokhtuev et al.

(10) Patent No.: US 7,416,701 B2
(45) Date of Patent: Aug. 26, 2008

(54) CALIBRATOR FOR FLUOROSENSOR

(75) Inventors: Eugene Tokhtuev, Duluth, MN (US);
Anatoly Skirda, Duluth, MN (US);
Viktor Slobodyan, Duluth, MN (US);
Christopher Owen, Duluth, MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 11/299,784

(22) Filed: Dec. 13, 2005

(65) Prior Publication Data

US 2006/0121614 A1 Jun. 8, 2006

Related U.S. Application Data

(62) Division of application No. 10/241,451, filed on Sep. 12, 2002, now Pat. No. 7,198,755.

(60) Provisional application No. 60/318,338, filed on Sep. 12, 2001.

(51) Int. Cl.
*G01N 21/64* (2006.01)
*G01N 21/66* (2006.01)
*G01N 15/06* (2006.01)
*G01N 33/00* (2006.01)
*C12Q 1/68* (2006.01)

(52) U.S. Cl. ............... 422/82.08; 422/50; 422/68.1; 422/82.05; 422/82.06; 422/82.07; 422/82.09; 422/82.11; 436/164; 356/432; 356/213; 29/592.1; 29/592

(58) Field of Classification Search ............ 422/50, 422/68.1, 82.05, 82.06, 82.07, 82.08, 82.09, 422/82.11; 436/164; 356/432, 213; 29/592.1, 29/592
See application file for complete search history.

(56) References Cited

U.S. PATENT DOCUMENTS

| | | | | |
|---|---|---|---|---|
| 4,084,905 A | * | 4/1978 | Schreiber et al. | ............ 356/317 |
| 4,394,573 A | | 7/1983 | Correa et al. | |
| 4,458,518 A | * | 7/1984 | Ingle | .......................... 73/1.88 |

(Continued)

FOREIGN PATENT DOCUMENTS

JP  2001228139  8/2001

OTHER PUBLICATIONS

U.S. Appl. No. 11/809,208, filed May 31, 2007, entitled, UV Fluorometric Sensor and Method for Using the Same, Tokhtuev et al.

*Primary Examiner*—Brian Sines
(74) *Attorney, Agent, or Firm*—Shumaker & Sieffert, P.A.

(57) ABSTRACT

A multichannel fluorosensor includes an optical module and an electronic module combined in a watertight housing with an underwater connector. The fluorosensor has an integral calibrator for periodical sensitivity validation of the fluorosensor. The optical module has one or several excitation channels and one or several emission channels that use a mutual focusing system. To increase efficiency, the excitation and emission channels each have a micro-collimator made with one or more ball lenses. Each excitation channel has a light emitting diode and an optical filter. Each emission channel has a photodiode with a preamplifier and an optical filter. The electronic module connects directly to the optical module and includes a lock-in amplifier, a power supply and a controller with an A/D converter and a connector. The calibrator provides a response proportional to the excitation intensity, and matches with spectral parameter of fluorescence for the analyzed fluorescent substance.

16 Claims, 13 Drawing Sheets

U.S. PATENT DOCUMENTS

| | | | |
|---|---|---|---|
| 4,553,033 A * | 11/1985 | Hubble et al. | 250/353 |
| 4,707,747 A * | 11/1987 | Rockwell, III | 358/473 |
| 4,767,206 A | 8/1988 | Schwartz | |
| 4,791,056 A | 12/1988 | Sizto et al. | |
| 4,804,849 A | 2/1989 | Booth et al. | |
| 5,059,790 A | 10/1991 | Klainer et al. | |
| 5,242,869 A * | 9/1993 | Tarumi et al. | 501/56 |
| 5,414,258 A * | 5/1995 | Liang | 250/252.1 |
| 5,532,498 A * | 7/1996 | Umberger et al. | 250/551 |
| 5,680,110 A * | 10/1997 | Whisson | 340/613 |
| 5,689,110 A * | 11/1997 | Dietz et al. | 250/252.1 |
| 5,917,534 A * | 6/1999 | Rajeswaran | 347/238 |
| 5,932,860 A * | 8/1999 | Plesko | 235/454 |
| 6,097,084 A * | 8/2000 | Sano et al. | 257/678 |
| 6,348,965 B1 | 2/2002 | Palladino et al. | |
| 6,608,675 B1 * | 8/2003 | Ishikawa | 356/237.1 |
| 6,611,000 B2 * | 8/2003 | Tamura et al. | 257/80 |
| 6,977,729 B2 * | 12/2005 | Marquardt et al. | 356/436 |
| 7,038,191 B2 * | 5/2006 | Kare et al. | 250/227.11 |
| 7,198,755 B2 | 4/2007 | Tokhtuev et al. | |

* cited by examiner

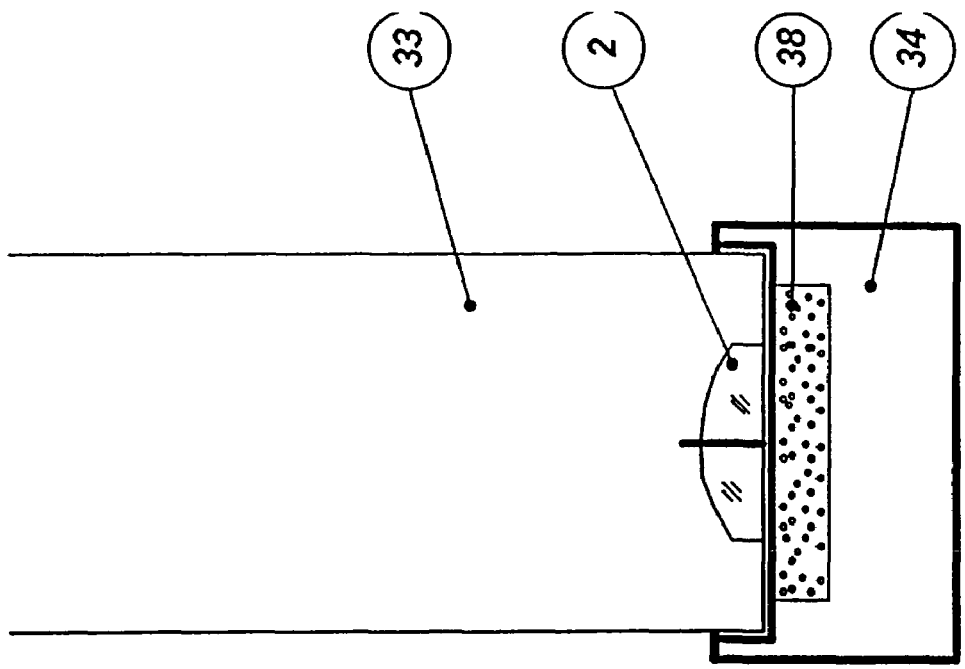
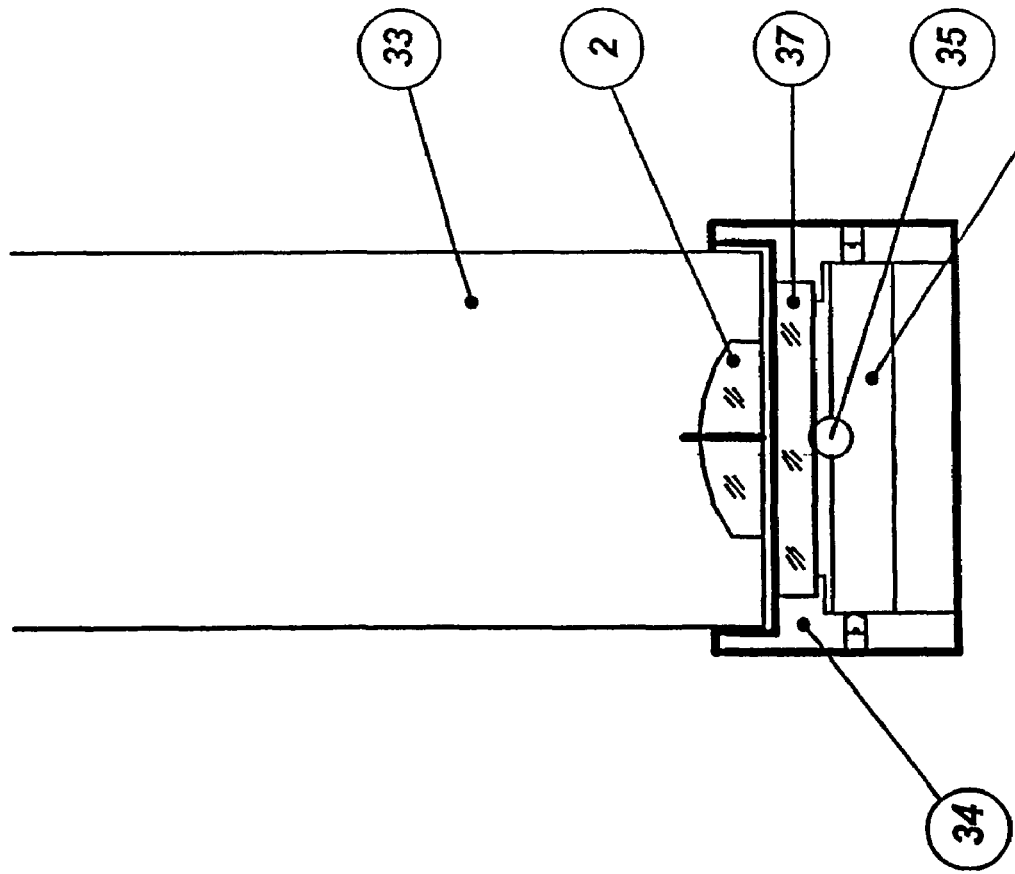
FIG. 8b
FIG. 8a

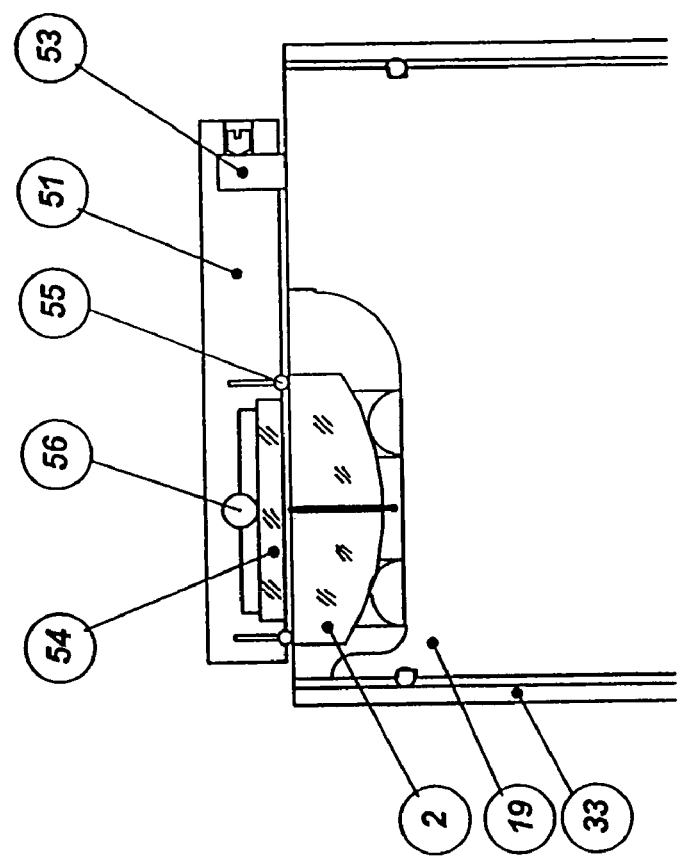
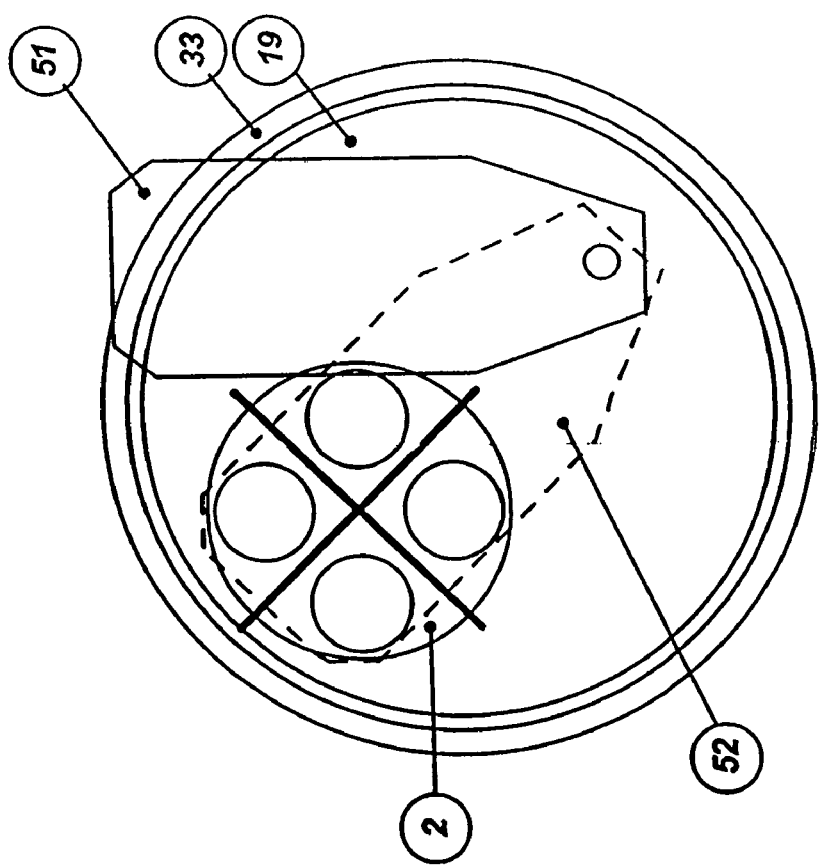
FIG. 10 b
FIG. 10 a

CALIBRATOR FOR FLUOROSENSOR

CROSS-REFERENCE TO RELATED APPLICATIONS

This application is a Divisional of U.S. application Ser. No. 10/241,451 filed on Sep. 12, 2002, now U.S. Pat. No. 7,198, 755. Priority is claimed from U.S. application Ser. No. 10/241,451 filed on Sep. 12, 2002 which claims the priority of provisional U.S. Application No. 60/318,338 filed Sep. 12, 2001, all of which is incorporated by reference.

BACKGROUND OF INVENTION

1. Technical Field

The invention relates generally to optical methods and apparatus for measuring fluorescent substances in liquids and more particularly to methods and devices for measuring the fluorescence of chlorophyll, dyes and optical backscatter in natural water or in different solvents.

2. Description of the Prior Art

Chlorophyll a is the most widely used indicator of algal biomass for the purposes of long-term monitoring and management programs, as well as short-term research studies. Its degradation products (i.e., phaeophytin a and phaeophoribide a) can be used to assess the physiological health of algae and its fluorescence properties can be related directly to chlorophyll a concentration. More recently, the biochemical/biophysical characteristics of the chlorophyll-fluorescence process have led to techniques, which in addition to more accurately estimating algal biomass, can almost instantaneously estimate the rate of algal photosynthesis (i.e., growth).

Current laboratory analysis of chlorophyll a requires intensive processing. In-field or rapid laboratory filtration for pigment concentration and extraction, with organic solvents, is required. In recent years chromatographic procedures (HPLC) have been used to accurately resolve individual pigments. Nevertheless, these methods are expensive, difficult, and are limited in their availability from commercial laboratories, with this method used by a relatively few research groups. Furthermore, at present, there appears to be little potential for this technique to be used in situ.

The most commonly utilized in-situ technologies for chlorophyll a determination are spectrophotometric and fluorometric methods of analysis. However, these methods contain absolute accuracy limitations due to relatively poor optical design, causing low spectral resolution for chlorophyll a. Problematic to these device development efforts is that absorption and emission maxims for chlorophylls band c are close to the peak of chlorophyll a, in the red region of the spectrum, allowing for errors to occur when these pigments constitute a significant proportion of the total chlorophyll content and correction for these interferences are not taken into account. Additional errors may be introduced by various accessory pigments and degradation products as well as humic acid and fulvic acid color, which also absorb and fluoresce at wavelengths similar to those for chlorophyll a, b and c, causing significant error when analyzed using broadband florescent techniques. In addition to accessory pigment interference, when utilizing broadband fluorometric analysis of photosynthetic pigments, significant error may also occur from optical backscatter (i.e., suspended inorganic and non-fluorescent organic particles). All of these interferences need to be taken into account during calibration and in the optical and electronic design of fluorometric probes. The claims as part of this present innovation describe a novel optical design that maybe utilized to increase the accuracy and specificity of fluorometric probes.

OBJECTS OF INVENTION

It is an object of the present invention to improve the optical sensor for measuring of fluorescence and increasing of sensitivity.

It is another object of the present invention to improve selectivity of the sensor to different fluorescent substances for example; chlorophyll a, chlorophyll b, chlorophyll c, that are simultaneously present in natural samples and to correct for interfering compounds, like optical backscatter, by direct measurement of these parameters.

It is a further objective of the present invention to provide a novel method for a periodical calibration of the multichannel fluorosensor in the laboratory and for direct testing in the field during deployment at depth.

Other objects and advantages of the present invention may be seen from the following detailed description.

SUMMARY OF INVENTION

In accordance with present invention the multichannel fluorosensor includes an optical module and an electronic module combined in a watertight housing with an underwater connector. In some embodiments the multichannel fluorosensor has an integral calibrator for periodical sensitivity validation of the fluorosensor.

The optical module has one or several excitation channels and one or several emission channels that use a mutual focusing system. To increase the efficiency of this mutual focusing system, each of the excitation and emission channels have a micro collimator made with one or several ball lenses. Each excitation channel has a light emitting diode and an optical filter and each emission channel has a photodiode with a preamplifier and an optical filter.

The electronic module is connected directly to the optical module and includes a lock-in amplifier, a power supply and a controller with an analog-to-digital (A/D) converter and a RS-232 type connector.

The calibrator provides a response, which is proportional to the excitation intensity and matches with spectral parameter of fluorescence for the analyzed fluorescent substance.

BRIEF DESCRIPTION OF THE DRAWINGS

FIGS. 8a and 8b are schematic drawings of the chlorophyll calibrator with a ruby ball lens.

FIGS. 10a and 10b are schematic drawings of an automatic cleaning system for the multichannel fluorosensor with the built-in ruby calibrator.

DETAILED DESCRIPTION OF THE INVENTION

Figure 1:
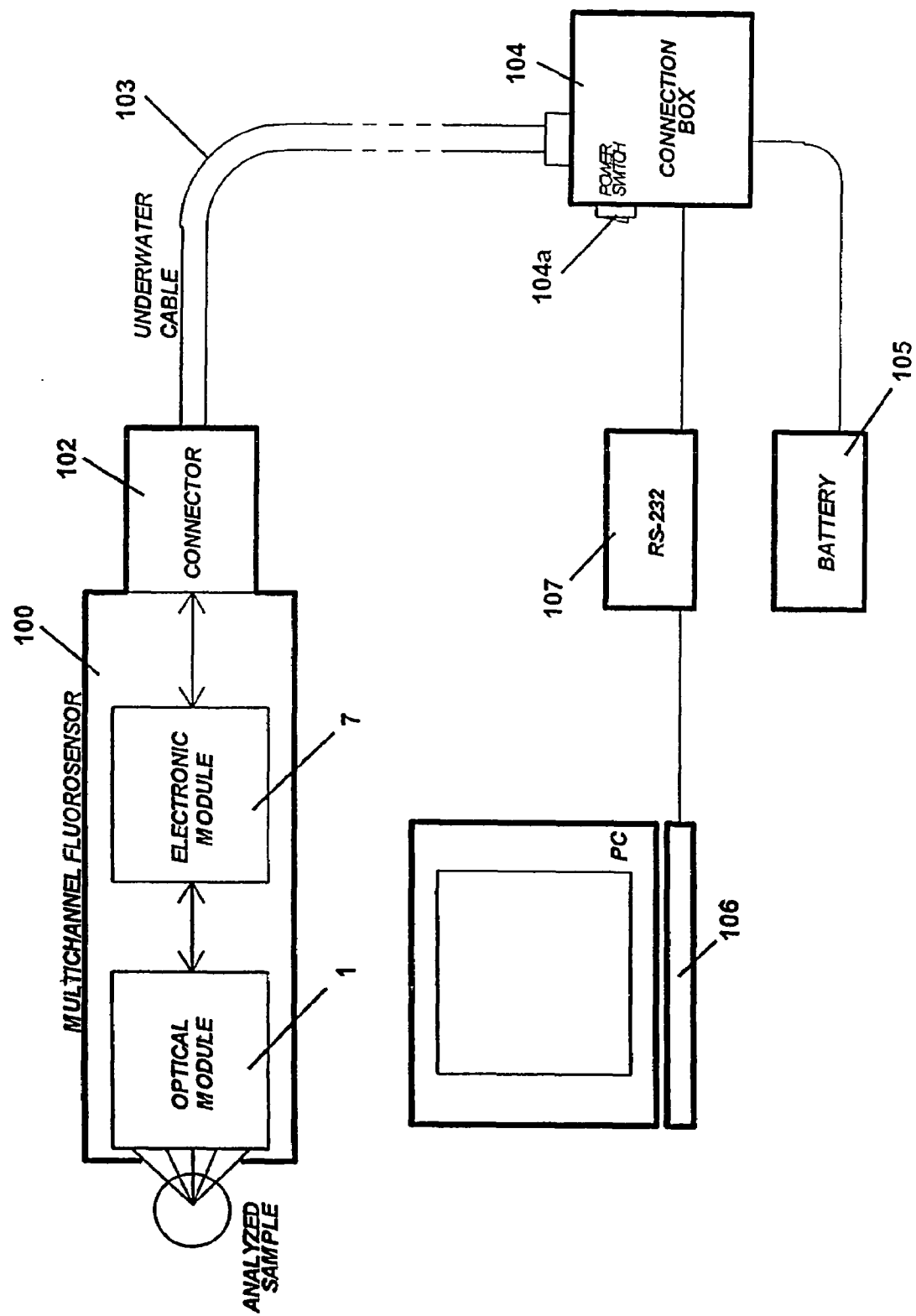
FIG. 1 is a block diagram of the multichannel fluorosensor and its connection to a personal computer.

The block diagram of the multichannel fluorosensor is shown on the FIG. 1. The multichannel fluorosensor 100 according to the present invention, has a watertight housing 101 with a watertight connector matched with a cable connector 102 on a underwater cable 103. The multichannel fluorosensor includes an optical module 1 with excitation channels and emission channels and an electronic module 7 with analog and digital electronics. The underwater cable allows analysis of fluorescent samples in the body of water at depths and has a connection box 104 with a power switch 104a. The connection box is connected to a battery 105 and to a data processing device 106 through a port 107. That implementation of such components as the data processing device 106 and the port 107 may be of any conventional type known to those of skill in the art. For example, the data processing device may be a personal computer (PC), a handheld PC, a personal data assistant (PDA) or other device that can operate as a data receiving, manipulating and displaying terminal. The possible implementations of the port 107 include but are not limited to RS-232, analog, SDI 12, and RS-485 devices.

Figure 2:
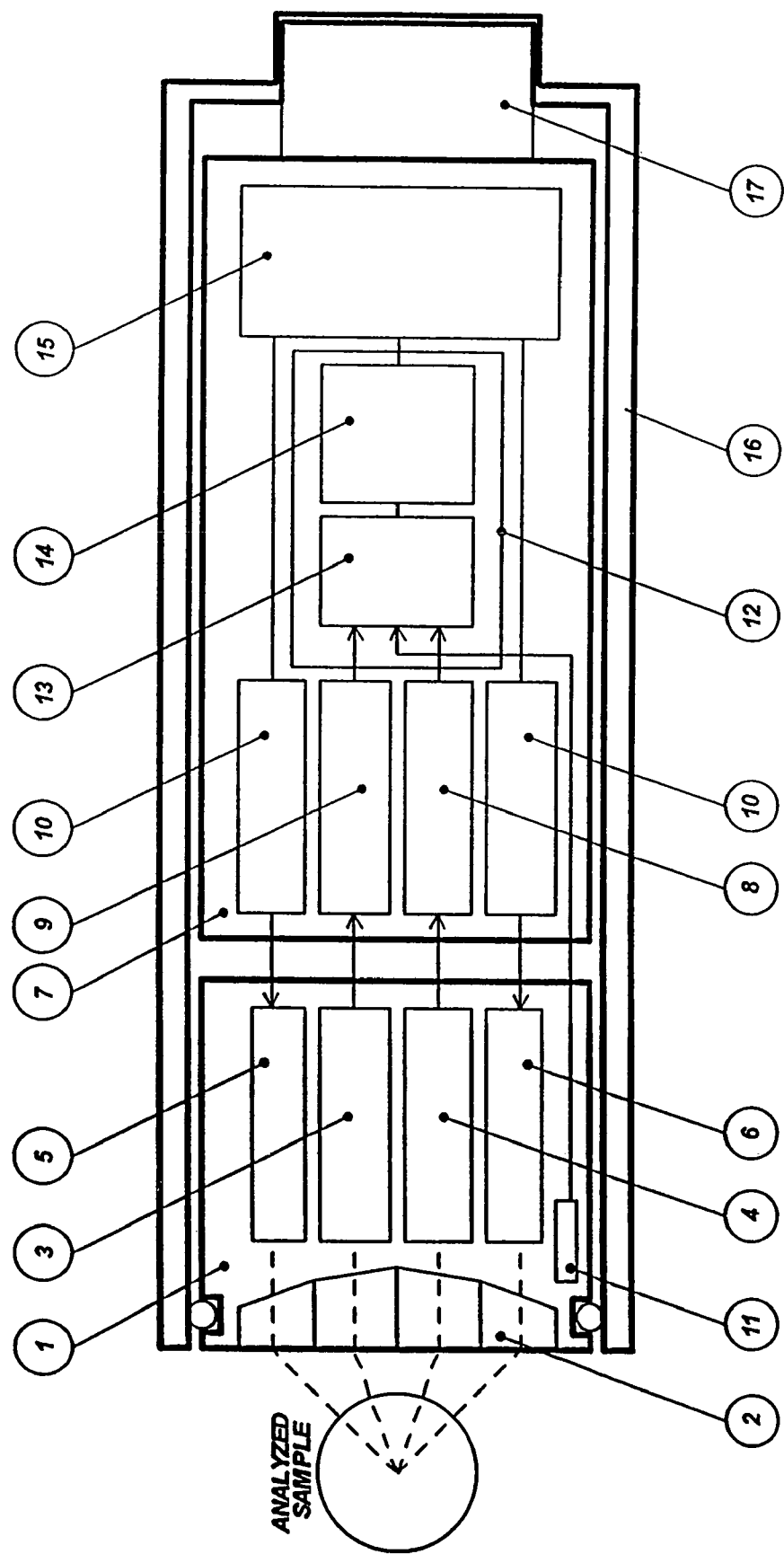
FIG. 2 is a schematic block diagram of the multichannel fluorosensor.

The detailed diagram of the multichannel fluorosensor is shown on the FIG. 2. The multichannel fluorosensor has the optical module 1 with a focusing system 2, emission channels 3,4 with optical filters, photodiodes- and preamplifiers, excitation channels 5,6 with optical filters and light emitting diodes (LEDs). The electronic module 7 includes lock-in amplifiers 8,9, generators 10 to modulate current through the light emitting diodes, temperature sensor 11, controller 12 having analog-to-digital converter (A/D) 13 to measure output signal of the emission channels and RS-232 device 14 to send data from the multichannel fluorosensor to the personal computer. The power supply 15 provides voltages for analog and digital electronics. Optical and electronic modules are placed inside the watertight housing 16 having a watertight connector 17.

Figure 3:
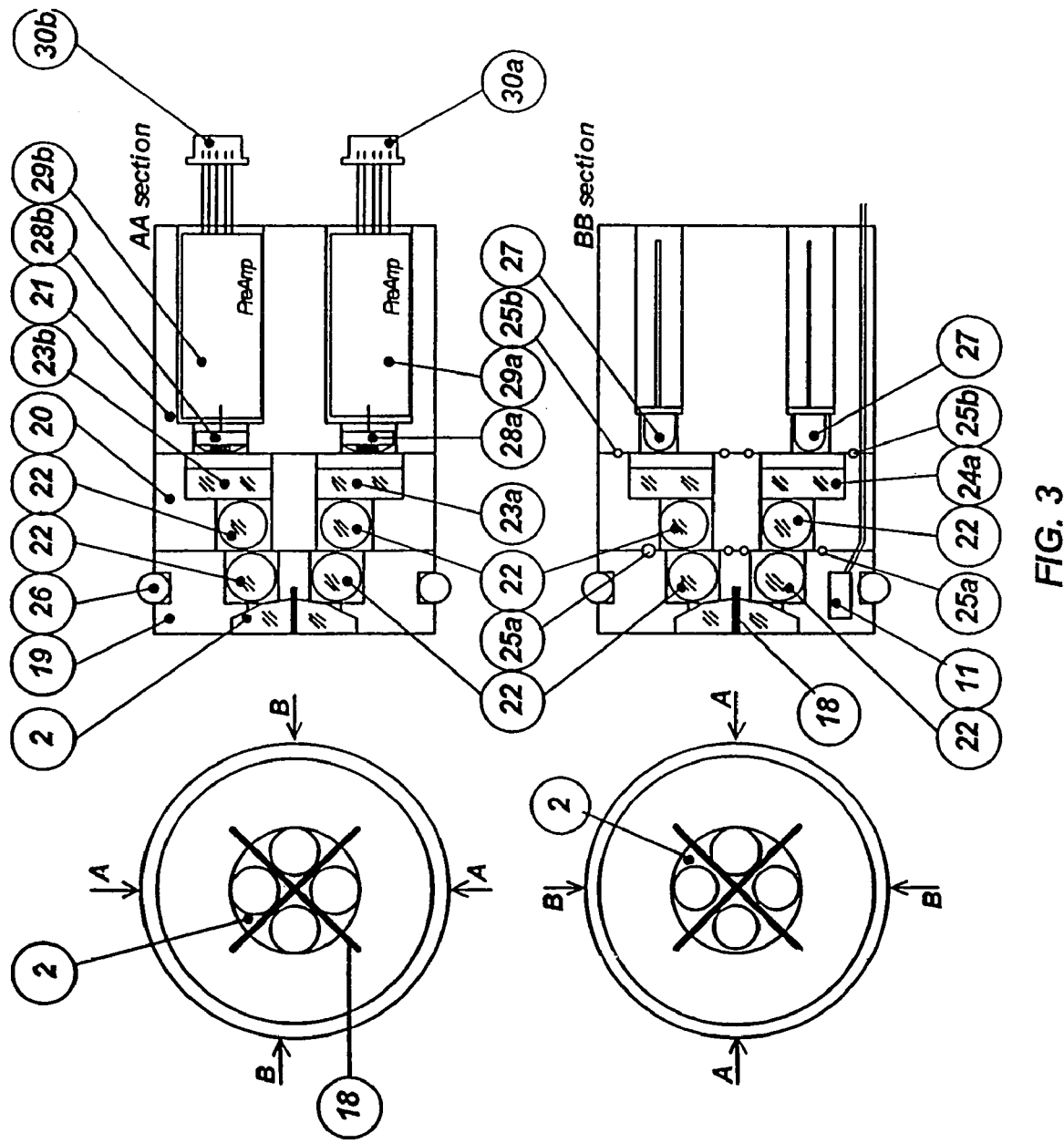
FIG. 3 is a schematic drawing of the optical module of the multichannel fluorosensor.

The schematic drawing of the optical module is shown in FIG. 3, wherein cross-sectional views AA and BB illustrate the structure of the excitation and emission channels. The shown variant of the optical module has two excitation channels (Section BB) and two emission channels (Section AA) that use the mutual focusing system 2. The focusing system 2 consists of a positive lens divided by and mounted onto opaque inserts 18 so as to provide optical separation between the channels. The opaque inserts 18 are mounted onto the front plate 19 so as to fix the focusing system 2 on the front plate via, in one embodiment, cuts made into the surrounding portions of a mounting hole for the positive lens of the focusing system 2. The front plate 19 is connected with a filter holder 20 and housing 21 for LEDs and photodiodes. Those three parts are made as separate units and connected together (using, for example, screws) so as to form separate channels for the optical and electronic parts. Excitation and emission channels have micro collimators made of ball lenses 22. Optical filters 23a, 23b, 24a, 24b are installed to provide spectral selection for excitation and emission wavelengths of analyzed substances. O-rings 25a, 25b are used for protection against the direct penetration of the excitation light into the emission channels. O-ring 26 is covered with an organic solvent resistant material (for example, Teflon®) and installed on the front plate of the optical module. The excitation channels have light emitting diodes 27, and emission channels have photodiodes 28a, 28b with preamplifiers 29a, 29b and connectors 30a, 30b.

Figure 4C:
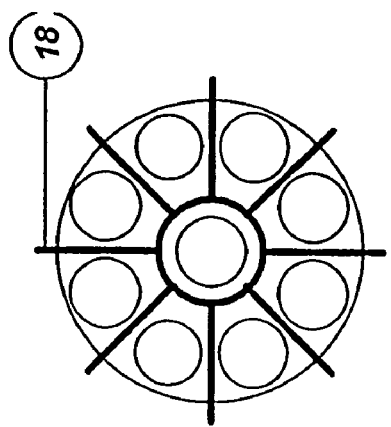
FIGS. 4a-4e are schematic drawings of other variants of the focusing systems for the optical module.
Figure 4B:
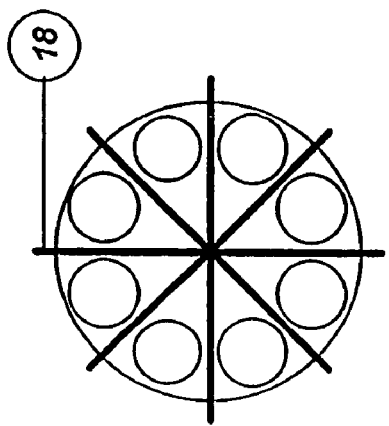
Figure 4A:
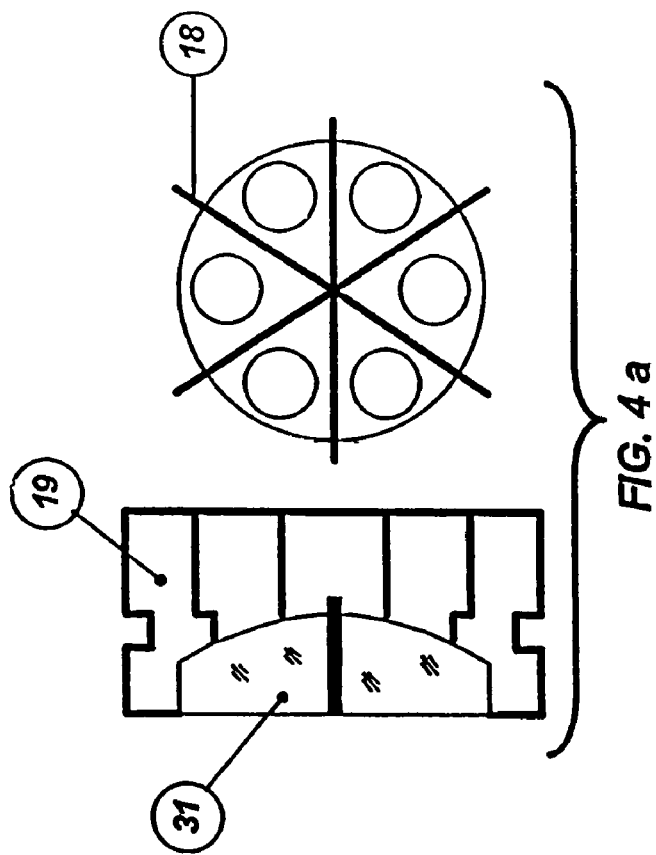
Figure 4:
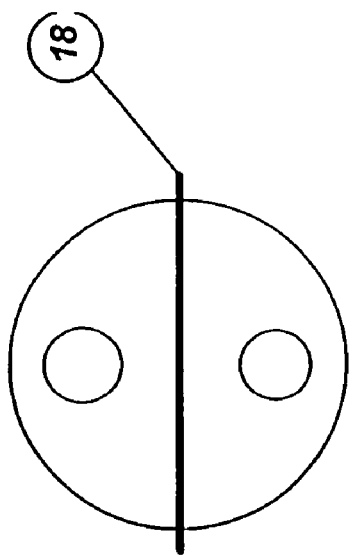
Figure 4:
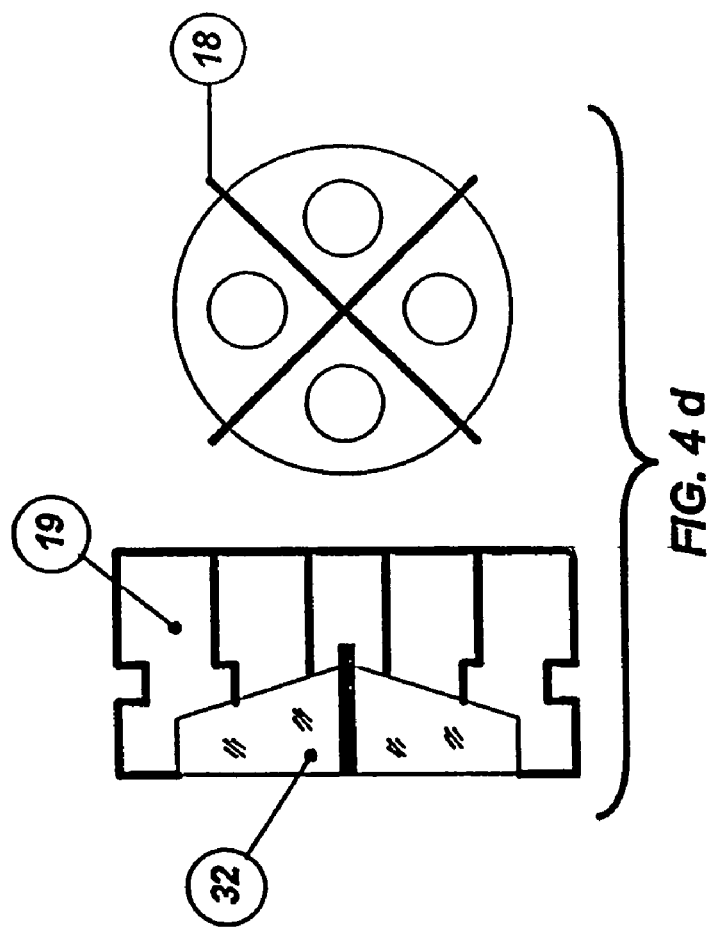

Variants of the focusing systems are shown the FIGS. 4a-4e. The focusing systems with six, eight and nine channels (FIGS. 4a, b, c) are shown as examples of lens focusing systems that may be implemented in the present invention. The positive lens 31 is glued into the front plate 19 and divided to form several separate optical channels separated by opaque inserts 18. Prismatic focusing systems shown at in FIGS. 4d and 4e are made of prismatic wedges 32 glued into the front plate of the optical module and cut to form several separate optical channels divided by opaque inserts 18. The cuts for the opaque inserts 18 should be deeper than thickness of the positive lens 31 or prismatic wedge 32 to provide total optical separation for optical channels. The optical design according to the present invention provides a number of optical channels focused at the same small volume because they are parts of the same positive lens 31 or prismatic wedge 32.

In another variation of the mutual focusing system, the separated optical channels are formed via at least two cylindrical holes tilted relative to the front plate and covered with optical filters therein such that the optical filters serve as windows. To optimize performance, the optical filters are installed to have an angle of incidence lower than 80°.

Figure 5:
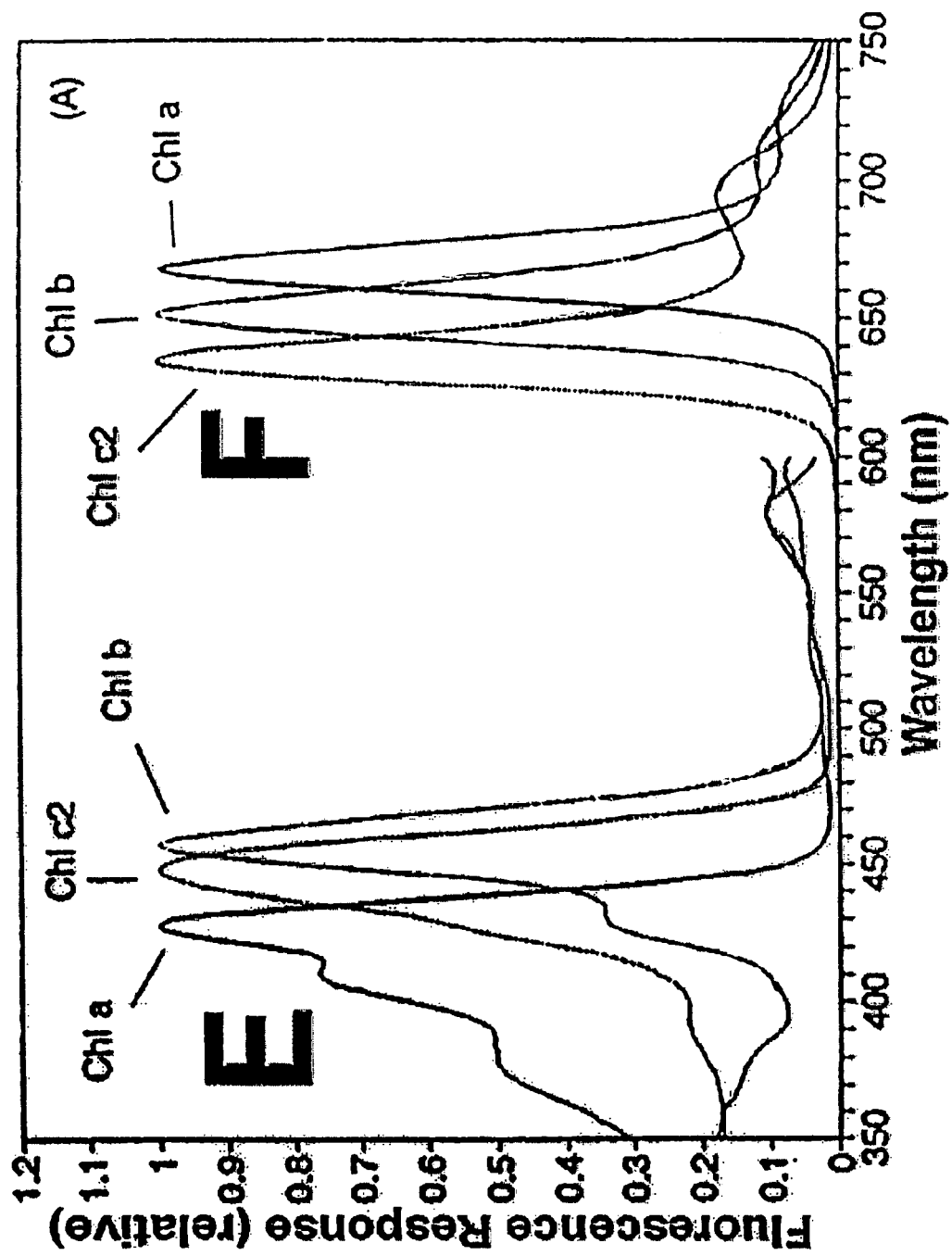
FIG. 5 is a graph showing typical fluorescence spectra of different chlorophyll constituencies in a 90% acetone solution.

The number of excitation and emission channels can be different when different components in a liquid composition need to be analyzed. Optimal spectral ranges for optical filters used in the multichannel fluorometer should be chosen after analyzing the fluorescent spectra of the components to provide the best sensitivity and selectivity. For example: chlorophyll a (Chl a), chlorophyll b (Chl b), chlorophyll c (Chl c), that are simultaneously present in samples could be measured separately using the difference in their excitation and emission spectra. FIG. 5 represents typical fluorescence spectra of different chlorophyll modification in 90% acetone solution, where E represents the excitation spectra and F represents the emission spectra. Optimal optical filters and recommended LEDs are shown in Table 1.

TABLE 1

Optimal optical filters and LEDs for measuring the different Chlorophyll modification after extraction in the 90% acetone

| Measured component | Excitation filter | Emission filter | Max LED emission | Type of LED |
|---|---|---|---|---|
| Chl a | 415 nm-440 nm | 665 nm-680 nm | 420 nm-435 nm | Jameco 137613 |
| Chl b | 455 nm-475 nm | 645 nm-665 nm | 450 nm-475 nm | MPJ 3900 mcd |
| Chl c | 435 nm-455 nm | 625 nm-645 nm | 435 nm-455 nm | Panasonic P389 |

Figure 6:
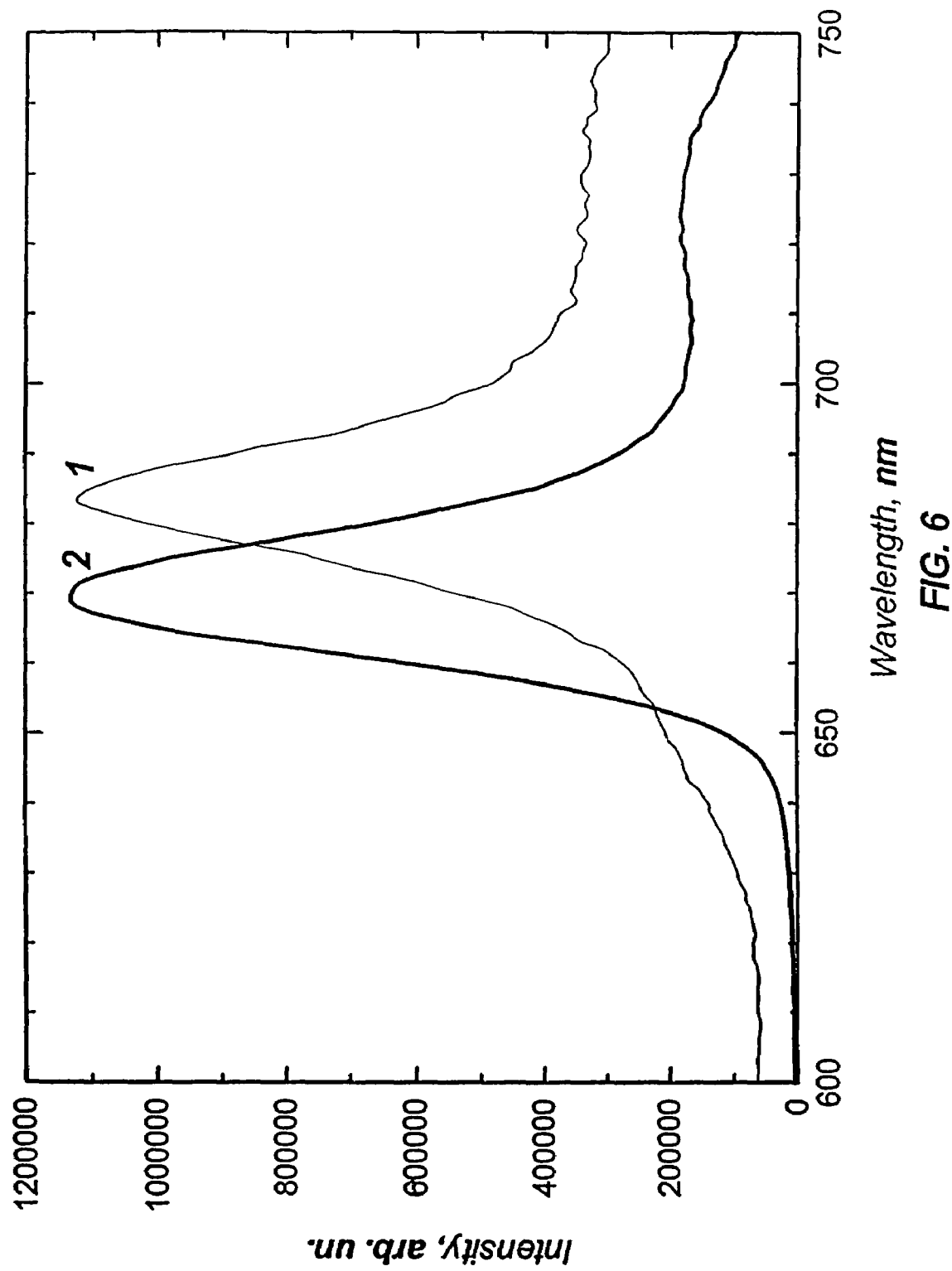
FIG. 6 is a graph showing typical fluorescence spectra of chlorophyll from an algae sample in water and in 90% acetone solution.

Another application of the multichannel fluorometer according to the present invention is the monitoring of chlorophyll a concentration in the body of water without sample preparation or chlorophyll a extraction. There are some differences in the optical design for such application because of different fluorescence spectra for extracted chlorophyll and for the living chlorophyll in-situ. Typical fluorescence spectra of chlorophyll from an algae sample in water and in 90% acetone solution are shown on the FIG. 6. The optimal emission filter for chlorophyll a in water would have a transmission band from 660 nm to 740 nm.

A significant error may occur from an optical backscatter (i.e., suspended inorganic and non-fluorescent organic particles). The backscattered excitation light not fully blocked by an emission filter gives a signal that is proportional to the particulate scatter from non-chlorophyll substances of the sample. Optical backscatter signal correction can be done by adding an optical backscatter channel in the multichannel fluorometer and subtracting the signal proportional to the optical back scatter from the signal of the fluorescent channel. The optical back scatter channel is built using a photodiode and emission filter with transmission in the transmission range of the excitation filter for the chlorophyll channel. Turbidity of the water sample can be also measured using an infrared method close to the recommendation of the International Standard ISO 7027 "Water Quality—Determination of Turbidity". According the ISO 7027, turbidity should be measured by measuring the scattered radiation at the wavelength 860 nm with bandwidth 60 nm. The multichannel fluorometer in at least embodiment has an excitation channel with an infrared GaAlAs LED having maximum emission at the wavelengths from 840 nm to 880 nm and emission channel with a GaAlAs photodiode having maximum sensitivity at the wavelengths from 840 nm to 880 nm. It is possible to use other LEDs and photodiodes with the appropriate band optical filters.

If the multichannel fluorosensor has an optical backscatter channel for turbidity measurements and turbidity correction it should be calibrated using a standard sample with known turbidity. The NIST traceable turbidity standard from APS Analytical Standards Inc. Redwood City, Calif. may be used, for example.

The multichannel fluorosensor according the present invention should be calibrated using solutions with known concentration of the chlorophyll. Methods of verifying the chlorophyll concentration in water samples are described in the following references, both of which are hereby incorporated herein by reference:

*Standard Methods For The Examination Of Water And Wastewater,* American Public Health Association. 1989, 17th ed. American Public Health Association, Washington D.C.

*Measuring Chlorophyll and Phaeophytin: Whom Should you Believe?,* Axler, R. P. and C. J. Owen. 1194, Lake and Reservoir. Management, 8(2): 143-151.

Figure 7:
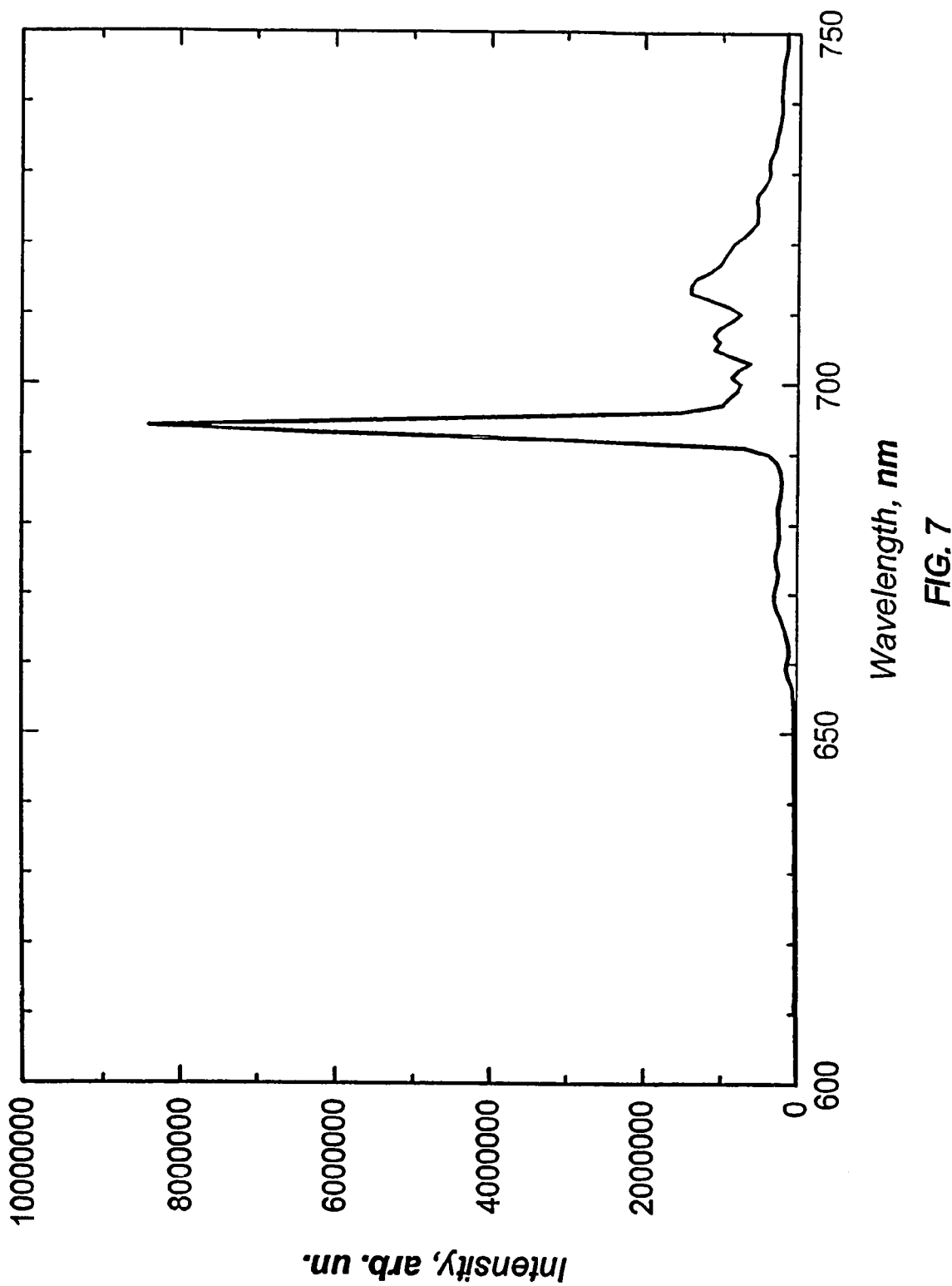
FIG. 7 is a graph showing typical fluorescence spectra of ruby.

The calibration validation of the multichannel fluorosensor can be done using a Rhodamine solution as a surrogate standard of fluorescence. The present inventions includes the use of a solid state calibrator for periodically testing the calibration of the multichannel fluorosensor. The calibrator according the present invention comprises a holder with one or several solid-state fluorescent elements. FIG. 7 shows typical fluorescence spectra of ruby. The fluorescent spectra of ruby begins at 650 nm, has a maximum near 690 nm and a broad band from 700 nm to 750 nm. The total distribution of fluorescent spectra of ruby is closer to the distribution of the fluorescent spectra of chlorophyll than the very broad band fluorescence of Rhodamine. The life time of Rhodamine standards is very limited contrary to unlimited life time for ruby standards.

Some embodiments of the chlorophyll calibrator with ruby according the present invention are shown in FIGS. 8a and 8b. The solid state calibrator with ruby ball lens (FIG. 8a) comprises holder 34 with the ruby ball lens 35 mounted at the adjustable disk holder 36. Window filter 37 is made of colored glass and placed in front of ruby ball lens for protection.

Another embodiment of the chlorophyll calibrator is shown on the FIG. 8b. Holder 34 has an epoxy disk 38 filled with ruby powder. Concentration of the ruby powder in the epoxy can be chosen to give a fluorescent response corresponding the specific chlorophyll concentration.

As described above, chlorophyll calibrators with a ruby ball lens or ruby powder filled epoxy are very stable and convenient in use. They work as a passive device that converts the light from the excitation channel into the emission channel by changing its spectral range to one similar to the spectral range of chlorophyll.

Figure 9A:
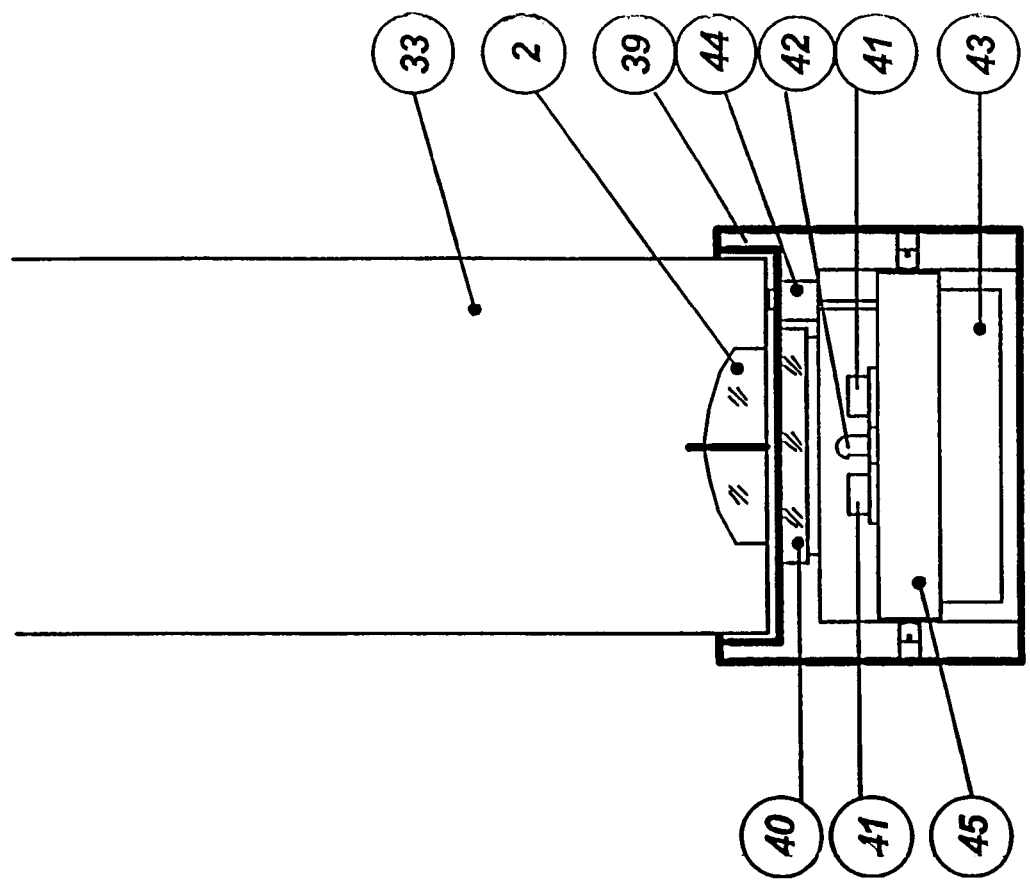
FIGS. 9a-9d are schematic drawings of the chlorophyll calibrator with a photodiode and a LED chlorophyll imitator.
Figure 9:
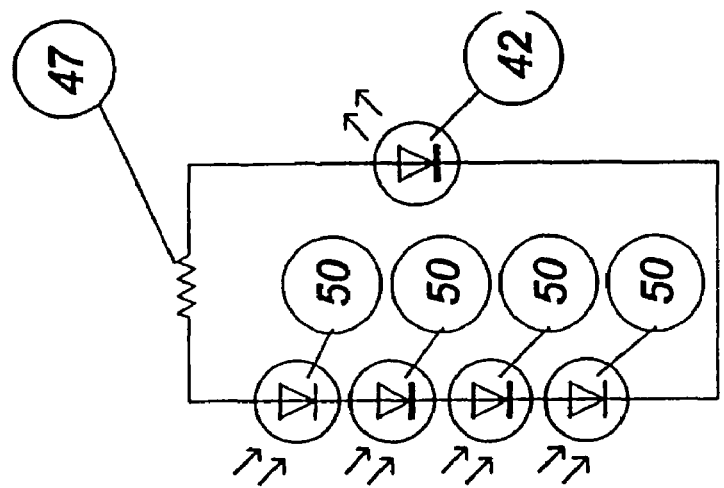
Figure 9:
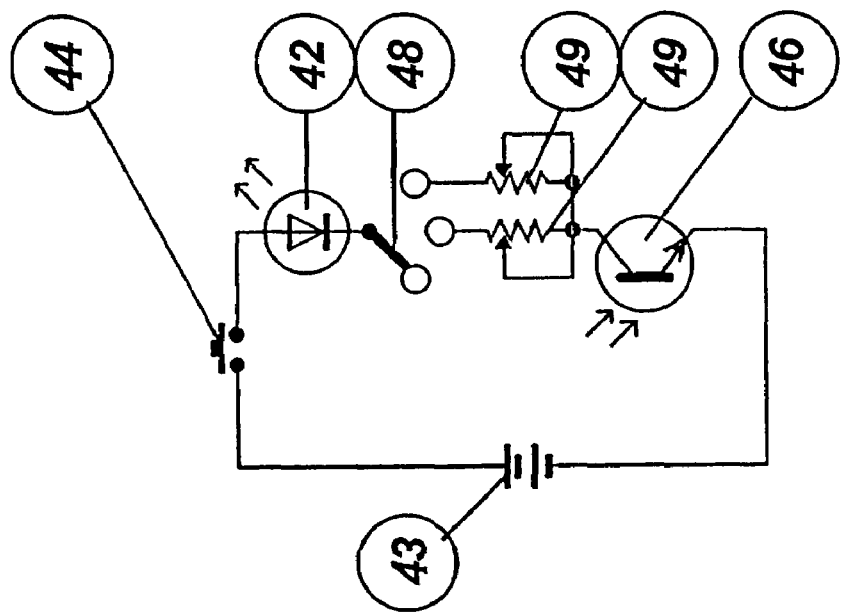
Figure 9:
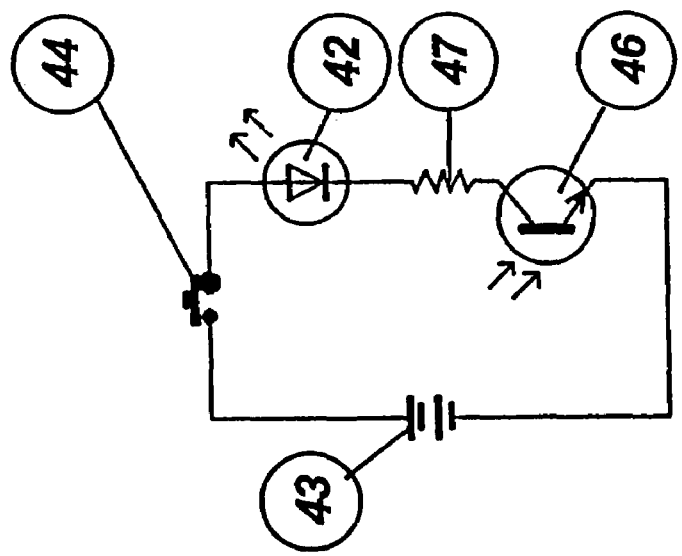

The active chlorophyll calibrator with photodetectors and a LED is shown at the FIG. 9a. It has the holder 39 with the window 40 and adjustable disk holder 45 carrying photodetectors 41, LED 42 and battery 43. A switch 44 is on the front surface of calibrator therein switch can be turned automatically ON when the multichannel fluorosensor is put on for calibration.

There are several variants of electronic schematics for the chlorophyll calibrator with photodetectors and LEDs according to present invention. FIG. 9b shows schematics which includes LED 42, battery 43, switch 44, phototransistor 46 and current limiting resistor 47. Said calibrator allows a user to regulate the readings generated when the multichannel fluorosensor is put in for calibration.

FIG. 9c shows schematic that allows to have several points of calibration. It includes LED 42, battery 43, switch 44, phototransistor 46, multiposition switch 48 and several adjustable resistors 49. This calibrator has several points of calibration, independently adjustable, to check calibration in the full range of operation of the multichannel fluorosensor.

FIG. 9d shows a schematic that includes several photodiodes 50 connected in series to receive a photocurrent passing through the LED 42. Resistor 47 works as a current limiting resistor. There is no battery needed. Said photodiodes can be segments of the multi element photodiode connected in series.

Though FIGS. 9a-9d illustrates implementations for the chlorophyll calibrators using photodetectors and LEDs, one of skill in the art given this disclosure of the present invention would understand that the above-mentioned implementations are but one way of achieving that component of the present invention and that there exist other optical, electromagnetic, infra-red, ultraviolet, microwave, RF or other energy transmission/detection systems that would be consistent with the present invention.

Optics for the multichannel fluorosensor can be contaminated during operation because of biofouling or deposition of impurities. FIG. 10a shows the multichannel fluorosensor 33 with the focusing system 2 having an automatic cleaning system 51 which has an open position and a closed position. The open automatic cleaning system position allows normal operation of the multichannel fluorosensor. The closed automatic cleaning system position 52 (shown with dotted line) protects focusing system from contamination while not in operation. According to the present invention the automatic cleaning system can be combined with a passive or active calibrator. FIG. 10b shows a automatic cleaning system for multichannel fluorosensor with the built-in ruby calibrator. Automatic cleaning system 51 actuated by rotating shaft 53 has a window 54 surrounded by soft protector 55 preventing the window from scratching during rotation. Said soft protector acts as cleaning agent during rotation and as sealing member covering the focusing system area while the multichannel fluorosensor is not in operation. There is a ruby ball lens mounted inside the automatic cleaning system after the window 54. When automatic cleaning system is in the closed position the ruby calibrator is centered in front of focusing system. This position allows the sensor calibration to be checked.

Figure 11:
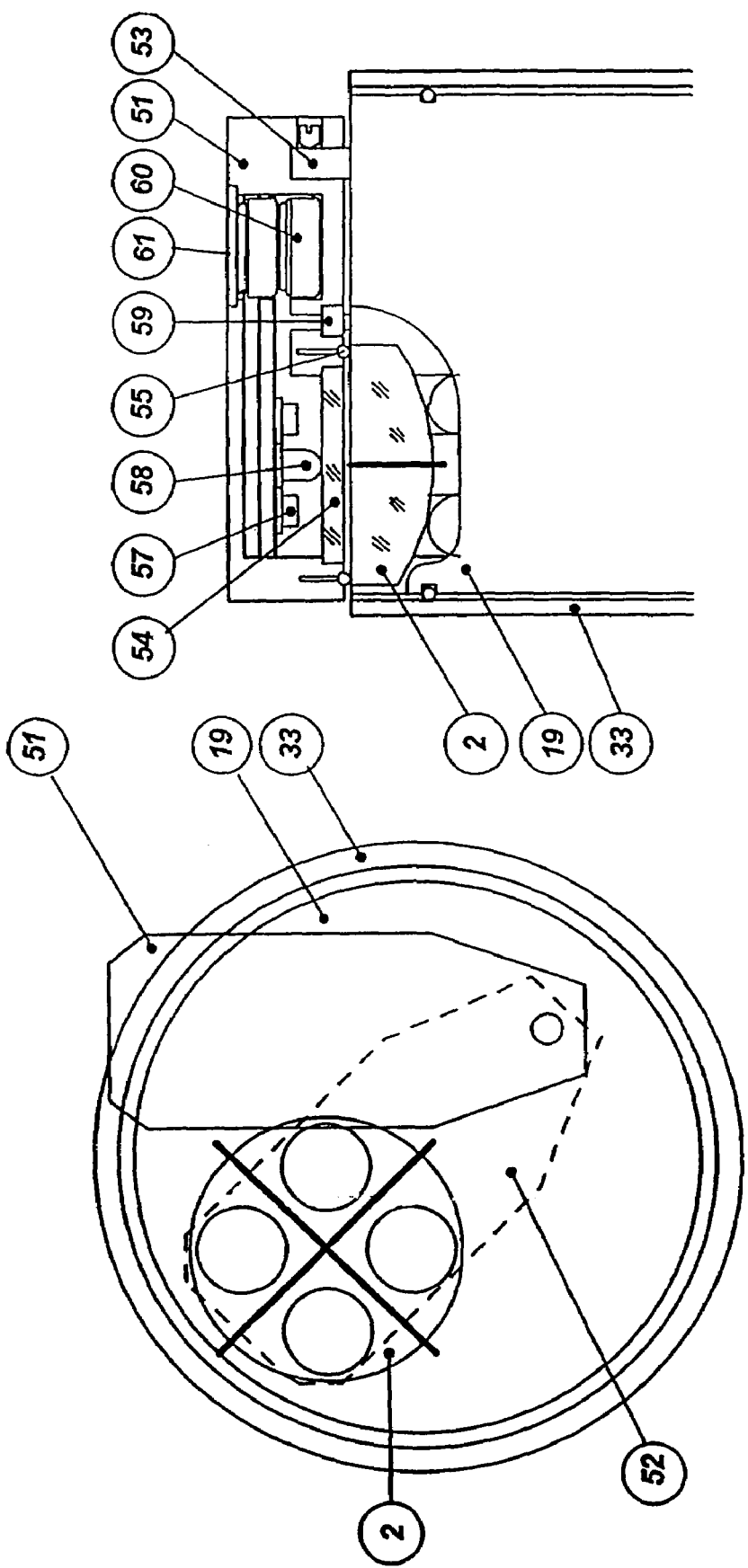
FIGS. 11a and 11b are schematic drawings of an automatic cleaning system for the multichannel fluorosensor with the built-in LED calibrator.

FIG. 11 shows an automatic cleaning system for the multichannel fluorosensor with a built-in LED calibrator. The focusing system 2 at the front end of multichannel fluorosensor 33 can be open for measurements when the automatic cleaning system 51 is in the open position or it can be covered and protected when the automatic cleaning system is in the closed position 52. The automatic cleaning system 51 actuated by rotating shaft 53 has a window 54 surrounded by soft protector 55. The window 54 covers a compartment with photodiodes 57 and LED 58. The open automatic cleaning system position allows normal operation of the multichannel fluorosensor. In the closed position of the automatic cleaning system, the switch 59 turns the electronics ON. The LED calibrator in this position is in front of the focusing system and sensor calibration can be verified. The switch 59 is a double action switch; to turn the electronics OFF, the calibrator should make one turn therein so as to press the switch 59 a second time. Battery 60 supplies power to the electronics. It is in a watertight compartment covered with a watertight lead 61.

The operation of the multichannel fluorosensor will be described hereinbelow using as an example of the multichannel fluorosensor with optical backscatter compensation for measuring the concentration of chlorophyll a in water. The multichannel fluorosensor, in this embodiment, has two identical excitation channels having light emitting diodes (LED) with a maximum emission between 430 nm and 480 nm and excitation optical filters with a transmission band from 410 nm to 490 nm. A first emission channel has a photodiode and optical filter with a transmission band from 660 nm to 740 nm and second emission channel has a photodiode and a optical filter having a transmission band from 430 nm to 480 nm.

Using two identical excitation channels two times increases the signal-to-noise ratio. The emission channel having transmission band from 660 nm to 740 nm measures the fluorescence signal from chlorophyll a in water. The emission channel having a transmission band from 430 nm to 480 nm measures the intensity of the scattered light which is proportional to the optical backscatter from non-chlorophyll particulate matter in the water sample. Optical backscatter from non-chlorophyll particulates generates a signal that is used for correction of the fluorescent signal to exclude the constituent of the fluorescent signal due to back-scattered signal from turbidity. There are two ball lenses in each of the emission and excitation channels to collimate light from the LEDs and to direct light from the focusing system to the photodiodes. The LEDs receive pulse current from the generators 10 (see FIG. 2) and emit light pulses in the blue spectral range. In each excitation channel (see FIG. 3), light from LED 27 passes through the excitation filter 24 then through two ball lenses 22 and through a segment of focusing system 2 limited by appropriate opaque inserts 18. All segments of the focusing system 2 are the parts of the same lens therefore all excitation and emission channels are precisely focused at the same small volume in front of the focusing system. The fluorescence of substances in this small volume is delivered to photodiodes with high optical efficiency. The first emission channel delivers to the first photodiode 28*a* the fluorescent signal proportional to the chlorophyll a concentration. The second emission channel delivers to second photodiode 28*b* a scattered signal proportional to the optical backscatter water sample. Preamplifiers 29*a* and 29*b* amplify pulsed photocurrents from photodiodes and send pulsed voltage signals to the lock-in amplifiers 8 and 9 (see FIG. 2). Output signals from said lock-in amplifiers and from temperature sensor 11 connected to the inputs of the analog-to-digital converter (A/D) 13. Temperature measurements and temperature correction are very substantial because the fluorescence yield of chlorophyll shows significant variations with variations of temperature.

Other example implementations of the multichannel fluorosensor include one system that incorporates at least one excitation channel includes two light emitting diodes (LEDs) and excitation optical filters, and the at least one emission channel includes two photodiodes and emission optical filters. A first of the LEDs has a maximum emission between 420 nm and 440 nm with an excitation optical filter having a transmission band from 410 nm to 450 nm, a second of the LEDs has a maximum emission between 370 nm and 380 nm with an excitation optical filter having a transmission band from 360 nm to 390 nm, a first of the emission optical filters has a transmission band from 670 nm to 690 nm, and a second of the emission optical filters has a transmission band with a half bandwidth from 410 nm to 450 nm In another implementation, the multichannel fluorosensor incorporates at least one excitation channel that includes three light emitting diodes (LEDs) and excitation optical filters, and at least one emission channel that includes two photodiodes and emission optical filters. A first of the LEDs has a maximum emission between 420 nm and 435 nm with an excitation optical filter having a transmission band from 415 nm to 440 nm, a second of the LEDs has a maximum emission between 440 nm and 475 nm with an excitation optical filter having a transmission band from 435 nm to 455 nm, a third of the LEDs has a maximum emission between 450 nm and 475 nm with an excitation optical filter having a transmission band from 450 nm to 475 nm, a first of the emission optical filters has a transmission band from 625 nm to 645 nm, a second of the emission optical filters has a transmission band from 645 nm to 665 nm, and a third of the emission optical filters has a transmission band with a half bandwidth from 665 nm to 680 nm In a further implementation, the multichannel fluorosensor is formed to incorporate at least one excitation channel that includes two light emitting diodes (LEDs) and excitation optical filters, and at least one emission channel that includes two photodiodes and emission optical filters. A first of the LEDs has a maximum emission between 430 nm and 480 nm with an excitation optical filter having a transmission band from 410 nm to 490 nm, a second of the LEDs has a maximum emission between 840 nm and 880 nm, a first of the emission channels has an optical filter with a transmission band from 660 nm to 740 nm, and a second of the emission channels has a photodiode with a maximum sensitivity from 840 nm to 880 nm.

Voltages measured by the A/D converter 13 can be converted into actual chlorophyll, temperature, and turbidity readings according to the following equations:

$$\text{Temperature}(°C.)=54\times(V_t^{Temp}-0.325)$$

$$\text{Turbidity}(NTU)=74.6\times(V_t^{Turb}-V_0^{Turb})$$

$$\text{Chl } a(ppb)=K\times[(V_t^{Chl}-V_0^{Chl})-0.004\times(V_t^{Turb}-V_0^{Turb})]\times[1+0.011\times(\text{Temperature}(°C.)-20)]$$

where $V_t^{Temp}$=the voltage from the temperature channel, $V_t^{Turb}$=the voltage from turbidity channel, $V_0^{Turb}$=the voltage from turbidity channel at zero (0) NTU, $V_t^{Chl}$=the voltage from chlorophyll channel, $V_0^{Chl}$=the voltage from chlorophyll channel at zero (0) ppb, K=a calibration constant equals 170 for chlorophyll a in water.

Calibration coefficients in the equations above represent just a example of calibration for a specific multichannel fluorosensor optimized for measuring chlorophyll a in water with correction of signal variation due to temperature variation and turbidity correction.

Although the present invention has been fully described in connection with the preferred embodiment thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed:

1. A calibrator for a fluorosensor, comprising:
   a holder that aligns the fluorosensor to receive a calibration beam;
   at least one photodetector, wherein the holder further aligns the photodetector to detect an excitation beam emitted by the fluorosensor, and wherein the photodetector provides an output signal based on an intensity of the detected excitation beam; and
   at least one light emitting diode (LED) that emits the calibration beam having an intensity proportional to the output signal of the photodetector and having a wavelength corresponding to at least one fluorescent wavelength emitted by a fluorescent substance to be analyzed.

2. The calibrator of claim 1, wherein the photodetector is a phototransistor.

3. The calibrator of claim 1, further comprising:
   a battery; and
   a switch that is turned on only during calibration of the fluorosensor.

4. The calibrator of claim 3, wherein the switch includes a multi-position switch and wherein the calibrator further includes at least one current limiting device.

5. The calibrator of claim 1, further including at least one adjustable resistor connected in series with the LED, wherein the adjustable resistor adjusts the calibration beam to one of a plurality of predetermined levels.

6. The calibrator of claim 1, wherein the photodetector includes at least one photodiode.

7. The calibrator of claim 6, wherein the photodetector includes a multi-element photodiode with elements connected in series.

8. The calibrator of claim 6, wherein the photodetector includes a plurality of silicon photodiodes connected in series with the at least one LED.

9. The calibrator of claim 1, wherein the at least one fluorescent wavelength is at least one of an infra-red, ultraviolet, or visible wavelength.

10. The calibrator of claim 1 wherein the fluorescent substance is a chlorophyll.

11. A device comprising:
    means for aligning a fluorosensor to receive a calibration beam;
    means for detecting an excitation beam emitted by the fluorosensor and for providing an output signal based on an intensity of the detected excitation beam; and
    means for emitting the calibration beam, the calibration beam having an intensity proportional to the output signal and having a wavelength corresponding to at least one fluorescent wavelength emitted by a fluorescent substance to be analyzed.

12. The device of claim 11 wherein the means for detecting an excitation beam comprises at least one of a photodetector, a phototransistor or a photodiode.

13. The device of claim 11 wherein the means for emitting the calibration beam comprises at least one light emitting diode (LED).

14. The device of claim 11 wherein the fluorosensor measures the fluorescence of the fluorescent substance to be analyzed.

15. The device of claim 11 wherein the fluorescent substance to be analyzed is a chlorophyll.

16. The device of claim 11 further including at least one current limiting resistor.

* * * * *